United States Patent
Ferree

(12) 
(10) Patent No.: US 6,248,106 B1
(45) Date of Patent: Jun. 19, 2001

(54) CROSS-COUPLED VERTEBRAL STABILIZERS

(76) Inventor: Bret Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

(21) Appl. No.: 09/513,127

(22) Filed: Feb. 25, 2000

(51) Int. Cl.$^7$ ............................................. A61B 17/56
(52) U.S. Cl. ................................................. 606/61
(58) Field of Search ........................... 606/60, 61, 72, 606/74, 59, 103

(56) References Cited

U.S. PATENT DOCUMENTS

| | | |
|---|---|---|
| Re. 36,221 | 6/1999 | Breard et al. . |
| 3,997,138 | 12/1976 | Crock et al. . |
| 4,146,022 * | 3/1979 | Johnson et al. .......................... 606/74 |
| 4,854,304 | 8/1989 | Zielke . |
| 4,966,600 | 10/1990 | Songer et al. . |
| 5,092,867 * | 3/1992 | Harms et al. ............................ 606/61 |
| 5,108,397 * | 4/1992 | White ...................................... 606/60 |
| 5,342,361 * | 8/1994 | Yuan et al. .............................. 606/61 |
| 5,352,224 * | 10/1994 | Westermann ............................ 606/61 |
| 5,387,213 | 2/1995 | Breard et al. . |
| 5,423,820 | 6/1995 | Miller et al. . |
| 5,496,318 | 3/1996 | Howland et al. . |
| 5,611,801 | 3/1997 | Songer . |
| 5,702,399 | 12/1997 | Kilpela et al. . |
| 5,704,936 | 1/1998 | Mazel . |
| 5,725,582 | 3/1998 | Bevan et al. . |
| 5,904,682 | 5/1999 | Rogozinski . |
| 5,964,769 | 10/1999 | Wagner et al. . |
| 5,989,256 | 11/1999 | Kuslich et al. . |
| 5,993,448 * | 11/1999 | Remmler ................................. 606/70 |
| 5,997,542 | 12/1999 | Burke . |

* cited by examiner

Primary Examiner—Gene Mancene
Assistant Examiner—Eduardo C. Robert
(74) Attorney, Agent, or Firm—Gifford, Krass, Groh, Sprinkle, Anderson & Citkowski, PC

(57) ABSTRACT

Spinal stabilization mechanisms act to prevent lateral bending, extension, and rotation at the disc space. Two or more anchors at each vertebral level, and links at each level to both anchors at the other level result in a cross-braced arrangement that enhances compression and promotes fusion. In the preferred embodiment, the mechanism uses screws for placement in the vertebral bodies and cables are used to connect the screws. The cables pull the screws together, applying compression across the disc space. Bone graft, cages, or distracting plugs and the device to enhance fusion area would fill or cross the disc space. The bone graft, cages, etc. within the disc space are preferably used to resist compression. The device may be used in the cervical, thoracic, or lumbar spine. The device is preferably placed anteriorly, but could also be used posteriorly, with the screws directed through the vertebral body pedicles. The various components may be constructed of titanium, stainless steel, polymers, or a combination of such materials. The anchors preferably include a post protruding from the vertebra, and a cable-holders which fits over the post. The post may be threaded, in which case a nut would be used to tighten the holders, or the cable holders may be allowed to rotate, depending upon the position and/or application of the fasteners. The cable holders may use tunnels, tubes or outer grooves to the hold the cables in position. Devices may also be added to keep the links from crossing one another where they cross.

21 Claims, 4 Drawing Sheets

CROSS-COUPLED VERTEBRAL STABILIZERS

FIELD OF THE INVENTION

This invention relates generally to orthopedic spinal surgery and, in particular, to vertebral fixation methods and apparatus which provide multi-dimensional stability and apply compressive forces to enhance fusion.

BACKGROUND OF THE INVENTION

In surgeries involving spinal fixation, interbody cages are often used to restore disc space height, serve as a conduit for bone graft, and to help immobilize vertebrae undergoing fusion. Distracting the disc space prior to cage insertion restore disc space height. Distraction serves two important functions. First, it can decrease pressure on spinal nerves by increasing the size of the intervertebral foramen. Second, distraction increases tension on the annulus fibrosis which, in turn, increases the stability of the vertebra-cage-vertebra construct.

Presumably the annular tension decreases with time, thus weakening the construct. Furthermore, the annulus is weakened in many patients with severe degenerative disc disease. Given these and other deficiencies with annular tension, additional fixation is frequently added to increase the rigidity of the vertebra-cage combination.

Currently such additional fixation is inserted onto or into the posterior aspect of the spine. Thus, patients who have cages inserted from an anterior approach must undergo a second operation from the posterior aspect of the body. As might be expected, the second surgery increases patient morbidity, insurance costs, and delays return to work.

There are two ways to insert supplemental fixation through the same incision. One technique uses the interbody cages disclosed in my co-pending U.S. patent application Ser. No. 09/454,908, the entire contents of which are incorporated herein by reference. Posterior insertion allows the addition of supplemental fixation through the same incision.

A second solution employs fixation inserted through the anterior aspect of the spine. With known anterior lumbar spine fixation techniques, a combination of screws and rods or plates are inserted on the lateral side of the vertebrae from an anterior or lateral approach. The fixation is placed on the lateral aspect of the spine to avoid the aorta. Previous metal devices placed under the aorta have lead to aneurysms in some cases (Dunn Device). Unfortunately, a few patients have died from rupture of the aneurysms.

Lateral fixation is not ideal with interbody cages. First, lateral fixation cannot be used at the L5-S1 level. The iliac arteries cross the L5-S1 level anteriorly and laterally. Second, the vascular anatomy of many patients does not permit lateral fixation at the L4-L5 level. The majority of cages are inserted at the L4-L5 and L5-S1 levels. Third, cages are generally inserted in a directly anterior-to-posterior fashion with the patient in a supine position. Lateral instrumentation is difficult if not impossible in most patients in the supine position.

The system described in U.S. Pat. No. 5,904,682 uses two flat plates applied to screws placed bilaterally on either side of the disc space. The system does not use cables or diagonal bracing to resist rotational forces. In U.S. Pat. No. 4,854,304 screws laced in the side of the vertebral bodies are connected from a lateral approach. The screws are connected with a threaded rod. In 1964, A. F. Dwyer described a system using a single cable to connect screws placed on the lateral portion of the vertebral bodies. Dr. Dwyer connected a series of screws with one screw per vertebral body. The arrangement described in U.S. Pat. No. 4,854,304 is similar to Dr. Dwyer's system, but the cable is replaced with a threaded rod. Dr. Ziekle modified Dr. Dwyer's system in 1975, as set forth in U.S. Pat. No. 4,854,304.

Cables and tensioning devices are also well known in orthopedic spine surgery. References that use cables include U.S. Pat. Nos. 4,966,600; 5,423,820; 5,611,801; 5,702,399; 5,964,769; 5,997,542. None use diagonal members to enhance compression and resist lateral movement, however.

SUMMARY OF THE INVENTION

This invention is directed to spinal stabilization mechanisms operative to prevent lateral bending, extension, and rotation at the disc space. Broadly, the mechanism includes two or more anchors at each vertebral level, and links for each anchor at each level to both anchors at the other level, resulting in a cross-braced arrangement.

In the preferred embodiment, the mechanism uses screws for placement in the vertebral bodies and cables are used to connect the screws. The cables pull the screws together, applying compression across the disc space. Bone graft, cages, or distracting plugs and the device to enhance fusion area would fill or cross the disc space. The bone graft, cages, etc. within the disc space are preferably used to resist compression.

The device may be used in the cervical, thoracic, or lumbar spine. The device is preferably placed anteriorly, but could also be used posteriorly, with the screws directed through the vertebral body pedicles. The various components may be constructed of titanium, stainless steel, polymers, or a combination of such materials.

The anchors preferably include a post protruding from the vertebra, and a cable-holders which fits over the post. The post may be threaded, in which case a nut would be used to tighten the holders, or the cable holders may be allowed to rotate, depending upon the position and/or application of the fasteners. The cable holders may use tunnels, tubes or outer grooves to the hold the cables in position. Devices may also be added to keep the links from crossing one another where they cross.

DETAILED DESCRIPTION OF THE INVENTION

Figure 1A:
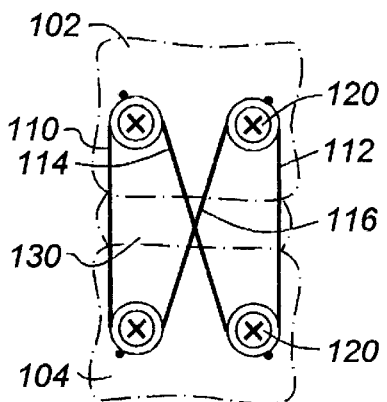
FIG. 1A is an anterior view of a cable-based cross-coupled vertebral stabilizing mechanism according to a preferred embodiment of the invention.
Figure 1B:
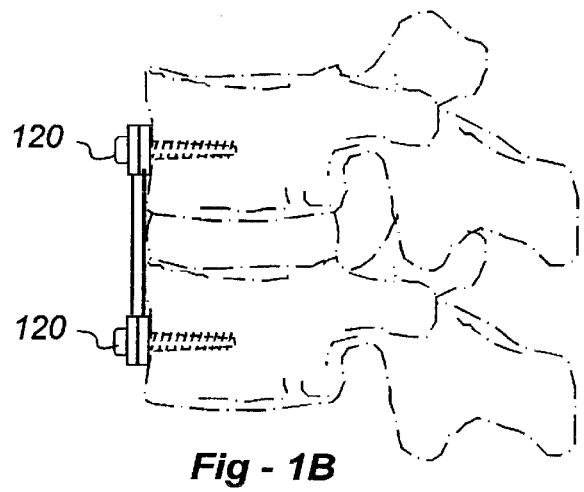
FIG. 1B is a drawing which shows the mechanism of FIG. 1A from a lateral perspective.

FIG. 1A is an anterior view of a cable-based cross-coupled vertebral stabilizing mechanism according to a preferred embodiment of the invention. FIG. 1B is a drawing which shows the mechanism of FIG. 1A from a lateral perspective. In this illustration, the mechanism is used to join upper and lower vertebrae 102 and 104, respectively, though the invention is applicable to multiple levels, as described elsewhere herein. It is assumed that some form of intervertebral cage and/or bone graft 130 is used in between the vertebrae 102 and 104 to resist compression. Broadly, the invention utilizes a pair of fasteners on each vertebrae, and elongated elements, preferably cables, in an axial and criss-crossed pattern to provide an arrangement that resists extension, lateral bending, and torsional/rotational stresses. As best seen in FIG. 1A, a preferred configuration utilizes a pair of screws 120 in the upper vertebrae, and a corresponding pair in the lower vertebrae, along with a pair of longitudinal cables 110 and 112, which are used in conjunction with a pair of crisscross cables 114 and 116.

Figure 2:
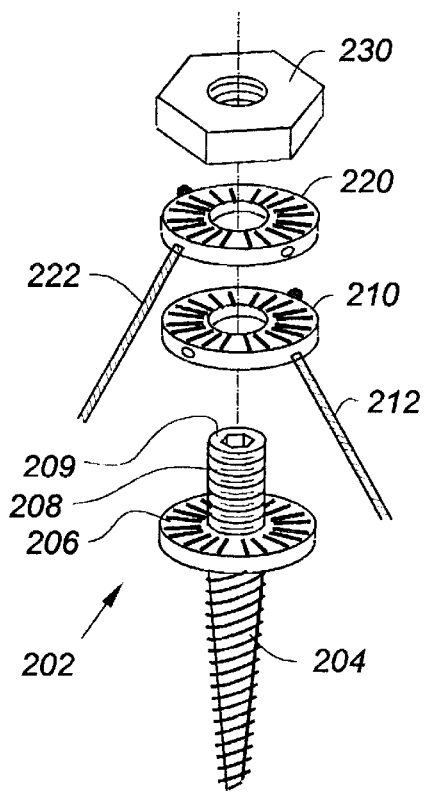
FIG. 2 is an oblique, exploded-view drawing of a cable holding and tensioner according to the invention.

The invention anticipates various apparatus for holding and tightening the cables or alternative members. FIG. 2 is an oblique, exploded-view drawing of a cable holding and tensioner according to the invention. In this configuration, a screw 202 features a threaded end 204, an exposed seating surface 206 and a threaded post 208, preferably including a tool receiving aperture 209 described in more detail below. A plurality of discs 210 and 220, each receiving a cable 212 and 222, respectively, are stacked onto the threaded post 208 and a nut 230 is tightened thereon as shown in the drawing, the seating surface 206, as well as the opposing surfaces of the discs 210 and 220 preferably include radial grooves or an alternative form of surface pattern or texture operative to resist rotation when the discs are stacked on top of one another and the fastener 230 tightened.

Figure 3:
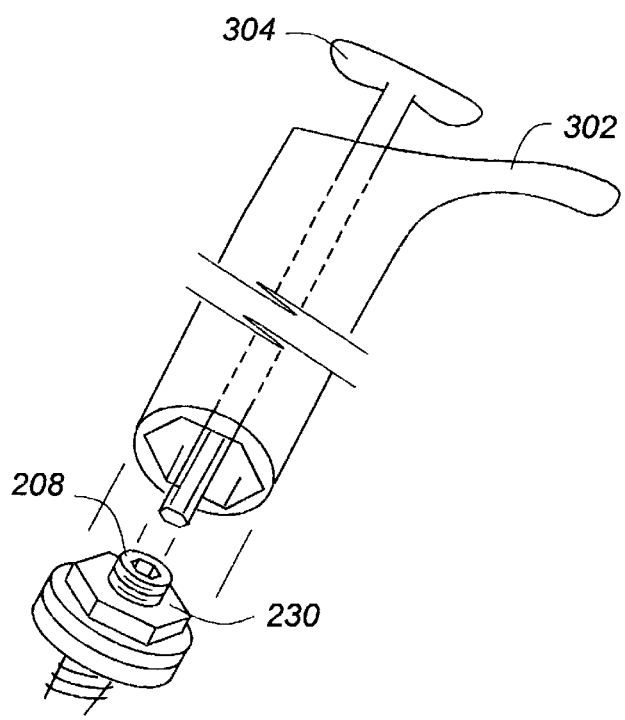
FIG. 3 is a drawing which shows a tool adapted to insert fasteners and tighten cable holders according to the invention.

FIG. 3 is a drawing which shows a tool adapted to insert fasteners and tighten cable holders according to the invention. Such a tool includes two elongated, independently rotating portions, including a nut tightening wrench 302 which fits over the locking nut 230 shown in FIG. 2, and a hex head screwdriver 304 which fits into the aperture 209 to prevent the screw from rotating while tightening the nut 230.

Figure 4A:
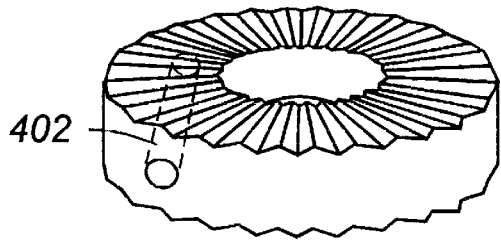
FIG. 4A is an oblique drawing of one type of blocking cable-receiving disc according to the invention.
Figure 4B:
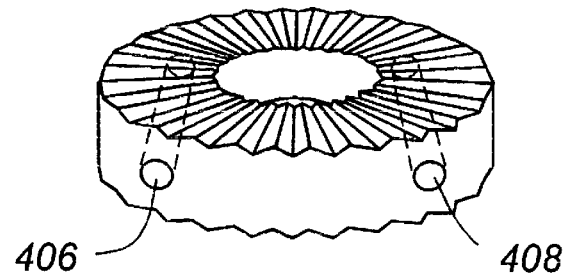
FIG. 4B is an oblique drawing of an alternative cable-receiving locking disc according to the invention.
Figure 4C:
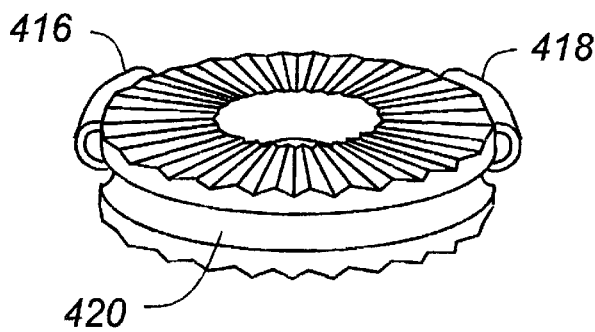
FIG. 4C illustrates yet a further alternative cable-receiving disc according to the invention.
Figure 5:
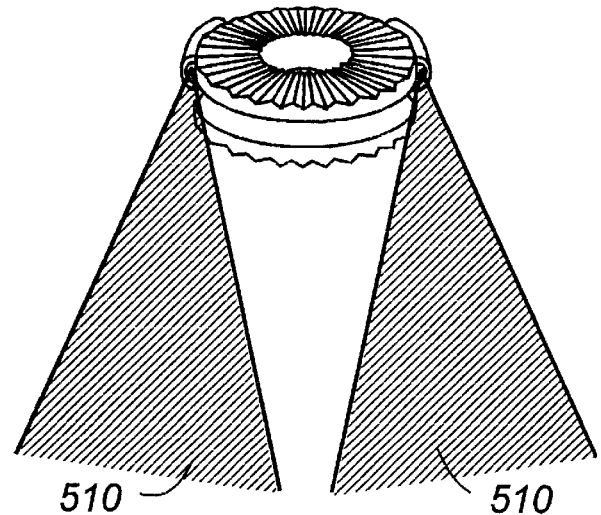
FIG. 5 is a drawing which shows how cable-receiving discs of the type shown in FIG. 4C allows a cable to move through a range of angles.

As mentioned above, the invention preferably utilizes different types of cable-receiving discs, depending upon placement and tensioning procedure. FIG. 4A is an oblique drawing of one type of blocking cable-receiving disc according to the invention. This particular disc includes a single aperture 402 through one side of the disc, which would require multiple discs to be stacked on each threaded post in a crisscross tensioning configuration. FIG. 4B is an oblique drawing of an alternative cable-receiving locking disc according to the invention. In this configuration, double cable-receiving apertures 406 and 408 are provided, preferably oriented along non-parallel lines, as shown. As in the case of the disc of FIG. 4A, the device would simply be turned over to provide a different desired cable orientation. FIG. 4C illustrates yet a further alternative cable-receiving disc according to the invention. With the device of FIG. 4C, one or more tubes 416 and 418 are provided, preferably along with a cable-receiving groove 420. As shown in FIG. 5, the device of FIG. 4C allows a cable to move through a range of angles 510 without creating an area with an acute bend or stress riser.

Figure 6:
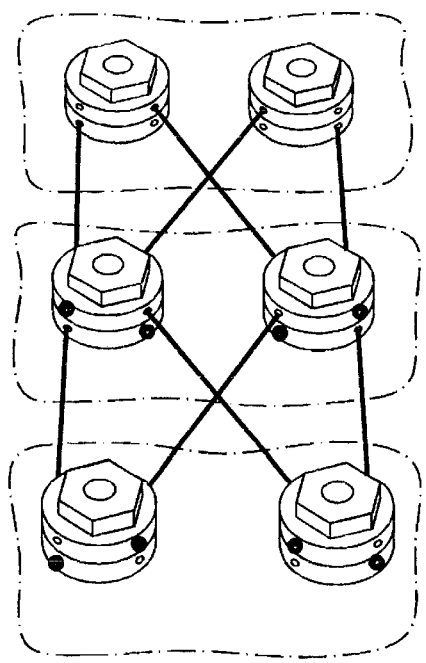
FIG. 6 is a drawing which shows how cable-receiving discs of the type shown in FIG. 4B may be stacked to join three or more vertebrae.
Figure 7:
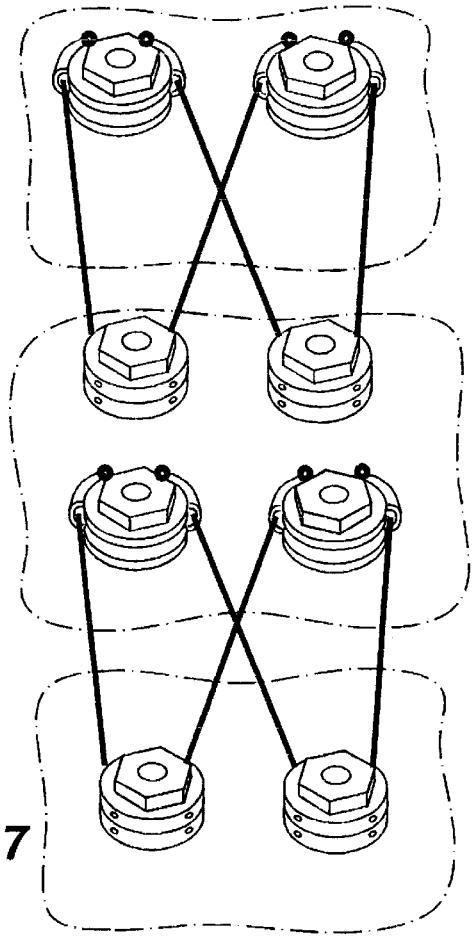
FIG. 7 is a drawing which shows how different types of cable-holding devices may be combined to join multiple vertebra.

The cable-receiving disc of FIG. 4B would be used in the same manner as that of FIG. 4A, though it should be evident that only one disc is required per fastener, as opposed to two. However, by stacking the cable-receiving discs of the type shown in FIG. 4B, more than two vertebrae levels may be joined with a minimum number of devices, and/or additional cables may be provided for added stability. FIG. 6 is a drawing which shows how cable-receiving discs of the type shown in FIG. 4B may be stacked to join three or more vertebrae. FIG. 7 shows how different types of cable-holding devices may be combined to join multiple vertebra. In this particular case, devices of type 4C are combined with those of FIG. 4A or 4B, with middle or intermediate vertebra (702) incorporating two sets fasteners.

Those of skill in the art of orthopaedic surgery will appreciate that certain of the tools and techniques used to tighten and secure the cable-holding bodies are known, and therefore do not necessarily form part of this invention. For example, tools of the type shown in FIG. 3 are available for related purposes, and may be used for the inventive purposes disclosed herein, perhaps with minor modification, as appropriate. In addition, known cable pulling/tensioning tools and cutting and crimping techniques used in orthopaedic surgery may also be applied to the instant invention, again, with any necessary modifications, as appropriate, to accommodate the physiology associated with the spine or particular level of the vertebrae.

Figure 8:
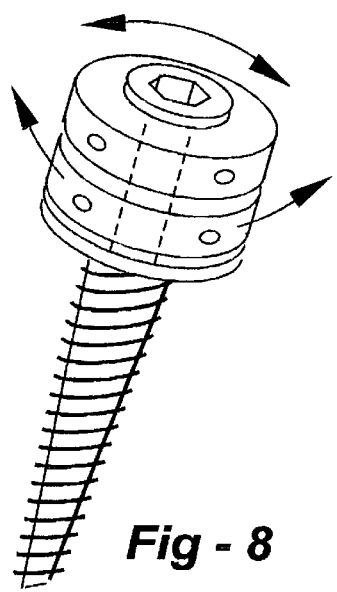
FIG. 8 shows how cable holders according to the invention may rotate around a respective post, in which case a tightening nut may not be necessary.

Although the cable-holding bodies of FIGS. 4A–4C preferably feature a friction-increasing upper and lower surfaces to resist rotation when tightened down, the cable holders may, instead, rotate around the post, as shown in FIG. 8, in which case a tightening nut would not be necessary. As a further alternative, the cables may be wound around a different type of holder similar to that in FIG. 4C, but without the cable-holding tubes. In this alternative embodiment, the grooves in the holder, which may or may not rotate, would include multiple cable-retainers 902, enabling a single crimp 904 to be used instead of separate crimping at each cable holder.

Figure 10:
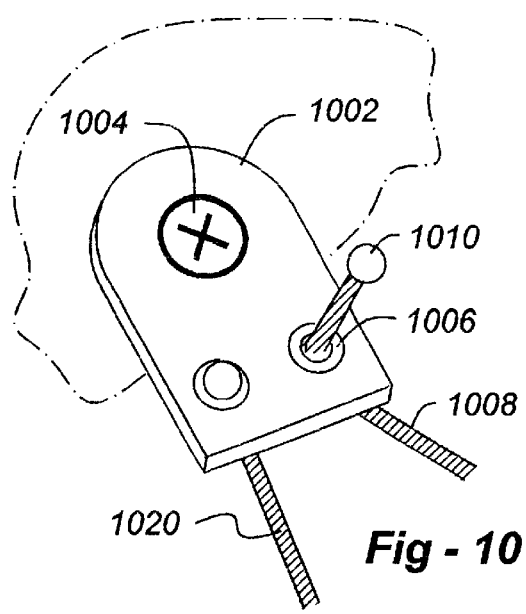
FIG. 10 is a drawing which shows an alternative fastener according to the invention affording an enhanced range of cable motion.

FIG. 10 is a drawing which shows an alternative cable holder according to the invention having a body 1002 attached to bone using a fastener 1004. One or more cable-receiving holes are provided and, in this case, the holes include cup-shaped recesses 1006. With such a configuration, a cable 1008 having a ball-shaped end 1010 is received by the recess, allowing the cable to more from side to side through rotation of the ball within the cup-shaped recess. Cable 1020 is shown having its ball-shaped end seated in the recess. As an alternative to a pre-formed ball an appropriately shaped crimp would also provide for an improved range of cable motion.

Figure 9:
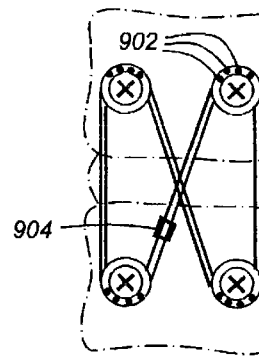
FIG. 9 illustrates how a single crimp may be used instead of separate crimping at each cable holder.
Figure 11:
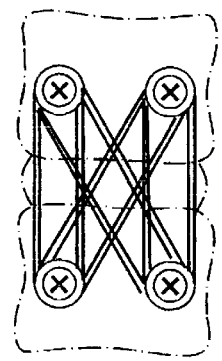
FIG. 11 is a drawing which shows how multiple cables or bands may be dressed from one fastener to another for enhanced security.

Multiple cables or elastic connectors may also be dressed from one fastener to another for enhanced stability, as shown in FIG. 11. For example, the holders of FIG. 4B may be stacked on each threaded post, enabling two cables to run from each fastener at each level. Alternatively, multiple holders of the type shown in FIG. 4C, or those shown in FIG. 9 may be stacked on each fastener post or, alternatively, a groove may be provided having a width sufficient to accommodate multiple cables or bands, and this may be permitted to rotate or lock into place, depending upon the situation at hand or preference of the surgeon.

To prevent injury to surrounding structures such as the aorta, devices according to the invention may be covered with a soft material such as siliastic. Fixation devices placed on the anterior aspect of the spine risk erosion into the aorta in the thoracic and lumbar spine regions, and in the esophagus in the cervical spine. The metal from plates or screws is unyielding, and as the aorta pulses into the metal a hole can form in the wall of the vessel. Discs may also herniated and anteriorily. In addition, bone spurs from the vertebrae can project anteriorily. At times, both this material and bone spurs may press against the aorta. This natural process does not injure the aorta or the esophagus, presumably because the soft disc material yields to the pulsations of aorta. Bone spurs probably reabsorb if they are causing injury to surrounding structures.

Figure 12:
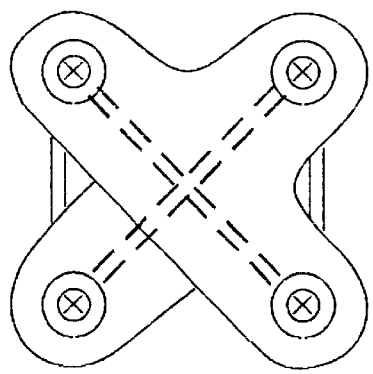
FIG. 12 shows how preformed sleeves may be placed over prominent portions of a mechanism according to the invention.

Devices according to the invention may be covered with soft materials such as silastic in one of two ways. First, preformed sleeves may be placed over prominent portions of the device, as shown in FIG. 12. Alternatively, liquid polymer may be poured over, or injected to surround the device. The material could be strengthened by inserting fibers into and around the device before or during the pouring or injection procedure. Polymer would be selected on the basis that it would cure rapidly and safely within the body.

Figure 13:
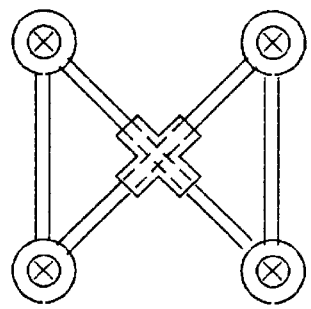
FIG. 13 depicts the use of additional devices for protecting cables from abrading one another where they cross.
Figure 14:
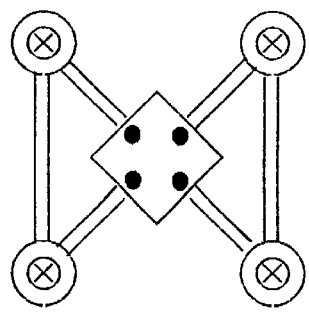
FIG. 14 is a drawing which illustrates the alternative use of a centerpiece with four cables attached thereto using screws or alternative fasteners.
Figure 15:
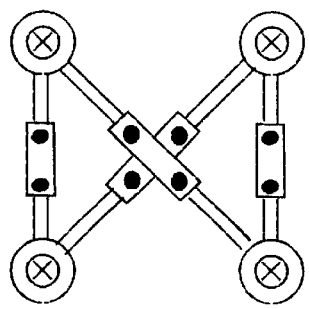
FIG. 15 is a drawing which illustrates the alternative use of turnbuckles on one or more cables.

Additional devices may be provided to protect the cables from abrading one another where they cross in the middle. For example, an x-shaped device with holes could be placed over the crossing wires, as shown in FIG. 13. Preferably, the wires would cross over the device in different planes to prevent friction with one another. Alternatively, a centerpiece could be used wherein four cables attached thereto using screws or alternative fasteners (FIG. 14). As yet a further alternative, as shown in FIG. 15, turn buckles could be incorporated into the cables or threaded rods to tighten them during installation or, perhaps as part of a postoperative or revision procedure.

The mechanisms described in the various embodiments of the invention offer several advantages over existing devices. The first, in contrast to current devices which do not permit compression, the inventive structure applies compression across the disc space. Compression is thought to increase the chances of a successful fusion. The inventive mechanism also allows the vertebrae to come together if the graft and or cage collapses or subsides; that is falls deeper into the body of the vertebrae. Many current devices hold the vertebrae apart when the graft collapses, which increases the chances of a pseudoarthrosis.

The inventive mechanism has a low profile, which may often allow placement under the aorta. A low profile is also beneficial in the cervical region of the spine. The inventive mechanism may also provide supplemental fixation within the body cages, which would increase the rigidity of the cage construct. Furthermore, devices according to the invention maintain compression across the disc space when the annular tension fails. As such, the inventive structures obviate a second, posterior operation to place screws and rods over the vertebrae.

Figure 16:
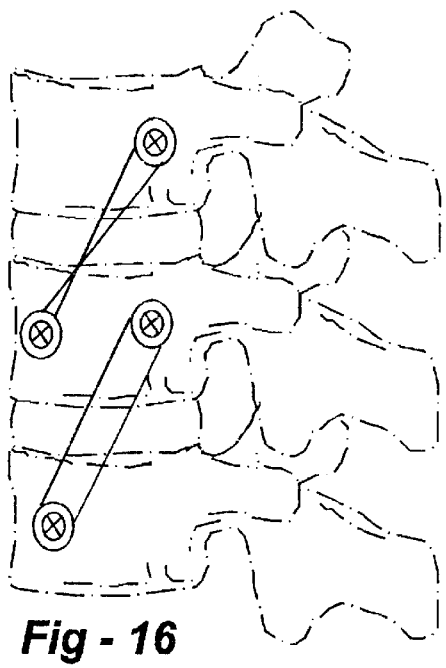
FIG. 16 is a drawing which shows how structures according to the invention may also be used to correct spinal deformities such as scoliosis.

Exact screw placement is made easier by virtue of the invention. Often screws are directed through plates placed on the spine, which make screw placement imprecise, leading to misdirected screws into adjacent disc spaces or laterally into the vertebrae. The device also affords the possibility of flexibility in patients with spinal deformities. As shown in FIG. 16, structures according to the invention may also be used to correct spinal deformities. For example, rotation of vertebrae would be more easily corrected using cables and cable holding devices according to the invention, in contrast to currently available appliances. Used on the sides of the vertebrae the cabling would correct for rotational deformities and easy insertion of current devices, should a surgeon wish to add rods and/or screws. In terms of the correction of spinal deformities, one could tighten the cable, or set of cables, to first to correct for scoliosis.

Another advantage is that additional levels of the spine may be added in subsequent surgeries without dismantling the entire device. That is, holding bolts may be removed, and new cable-holding bodies added, or, with grooves wide enough to permit multiple cables, new cabling alone may be added to multiple levels. The inventive mechanisms help hold in bone graft, cages or other devices to enhance fusion, while not stressing the "shield" of the bone graft.

I claim:

1. Apparatus for stabilizing upper and lower spinal vertebra, comprising:
    a first pair of right and left fasteners attachable to the upper vertebra;
    a second pair of right and left fasteners attachable to the lower vertebra;
    a first cable interconnecting the right fasteners;
    a second cable interconnecting the left fasteners;
    a third cable interconnecting the right fastener of the first pair with the left fastener of the second pair; and
    a fourth cable interconnecting the left fastener of the upper vertebra with the right fastener of the second pair.

2. The apparatus of claim 1, wherein the fasteners further include:
    a post adapted to protrude from the vertebra; and
    a cable-receiving body which fits over the post.

3. The apparatus of claim 2, wherein:
    the post is threaded; and
    a nut is used to tighten the cable-receiving body.

4. The apparatus of claim 3, wherein:
    the cable-receiving body has opposing outer surfaces, and one or both of the surfaces further includes a texture which keeps the body from rotating on the post when the nut is tightened.

5. The apparatus of claim 4, wherein the texture comprises a plurality of radially oriented grooves.

6. The apparatus of claim 1, wherein the cable-receiving body includes one or more cable-receiving apertures formed therethrough.

7. The apparatus of claim 1, wherein the cable-receiving body includes an outer groove to receive one or more cables.

8. The apparatus of claim 1, wherein the cable-receiving body includes one or more cable-receiving tubes.

9. The apparatus of claim 1, wherein the cable-receiving body includes one or more holes with a cup-shaped recess to receive a cable with a ball-shaped end.

10. The apparatus of claim 1, further including a device to keep the third and fourth cable s from touching one another.

11. The apparatus of claim 10, wherein the device to keep the third and fourth cables from touching one another is a body with spaced apart apertures to receive the third and fourth cables.

12. The apparatus of claim 10, wherein:

the third and fourth cables are separated midway along their lengths resulting in four free cable ends; and the device to keep the third and fourth cables from touching one another is a body to which the free ends attach.

13. The apparatus of claim 1, further including a covering to keep the third and fourth cables from touching one another or to protect surrounding soft anatomic structures.

14. The apparatus of claim 13, wherein the covering is polymeric.

15. The apparatus of claim 1, further including a turnbuckle associated with one or more of the cables.

16. The apparatus of claim 1, further including a plurality of cables from at least one fastener to another.

17. Apparatus for stabilizing spinal vertebra at two levels, comprising:

a first pair of anchors positioned side by side on a first level of said two levels and a second pair of anchors positioned side by side on a second level of said two levels threaded end penetrable into the vertebra, and a post which remains exposed;

at least one cable holder on each post; and at least one cable from each holder on each level to the two holders of the other level.

18. The apparatus of claim 17, wherein at least some of the cable holders are tightened onto the anchors.

19. The apparatus of claim 17, wherein the cable holders include one or more cable-receiving apertures formed therethrough.

20. The apparatus of claim 17, wherein the cable holders include an outer groove to receive one or more cables.

21. The apparatus of claim 17, further including a covering to keep the cables from touching one another or to protect surrounding soft anatomic structures.

* * * * *

UNITED STATES PATENT AND TRADEMARK OFFICE
CERTIFICATE OF CORRECTION

PATENT NO. : 6,248,106 B1
DATED : June 19, 2001
INVENTOR(S) : Bret Ferree

It is certified that error appears in the above-identified patent and that said Letters Patent is hereby corrected as shown below:

Column 8,
Line 8, after "levels" insert -- , each anchor having a --

Signed and Sealed this

Fourth Day of February, 2003

JAMES E. ROGAN
*Director of the United States Patent and Trademark Office*